(12) United States Patent
Sterett et al.

(10) Patent No.: US 6,565,570 B2
(45) Date of Patent: May 20, 2003

(54) BONE PLATE AND RETRACTOR ASSEMBLY

(75) Inventors: William Sterett, Edwards, CO (US); Kirk J. Bailey, Blairstown, NJ (US); Patrick Rousseau, Hardwick, NJ (US)

(73) Assignee: Electro-Biology, Inc., Parsippany, NJ (US)

( * ) Notice: Subject to any disclaimer, the term of this patent is extended or adjusted under 35 U.S.C. 154(b) by 0 days.

(21) Appl. No.: 09/808,260

(22) Filed: Mar. 14, 2001

(65) Prior Publication Data

US 2002/0133157 A1 Sep. 19, 2002

(51) Int. Cl.[7] .............................................. A61B 17/56
(52) U.S. Cl. .......................................................... 606/69
(58) Field of Search ........................... 606/69, 60, 72, 606/70, 71, 151, 104, 215

(56) References Cited

U.S. PATENT DOCUMENTS

| | | | |
|---|---|---|---|
| 1,769,525 A | 7/1930 | Maness | |
| 4,793,335 A | 12/1988 | Frey et al. | 128/92 R |
| 4,905,679 A * | 3/1990 | Morgan | |
| 4,944,739 A | 7/1990 | Torre | 606/53 |
| 5,053,039 A | 10/1991 | Hofmann et al. | 606/87 |
| 5,147,361 A * | 9/1992 | Ojima et al. | |
| 5,314,431 A | 5/1994 | Graziano | 606/101 |
| 5,324,290 A * | 6/1994 | Zdeblick et al. | |
| 5,474,553 A * | 12/1995 | Baumgart | |
| 5,613,969 A | 3/1997 | Jenkins, Jr. | 606/87 |
| 5,620,448 A | 4/1997 | Puddu | 606/87 |
| 5,722,978 A | 3/1998 | Jenkins, Jr. | 606/87 |
| 5,749,875 A * | 5/1998 | Puddu | |
| 5,827,286 A | 10/1998 | Incavo et al. | 606/71 |
| 5,964,763 A | 10/1999 | Incavo et al. | 606/71 |
| 5,980,526 A | 11/1999 | Johnson et al. | 606/86 |
| 6,008,433 A | 12/1999 | Stone | 623/16 |
| 6,159,217 A | 12/2000 | Robie et al. | 606/88 |
| 6,224,602 B1 * | 5/2001 | Hayes | |
| 6,235,032 B1 * | 5/2001 | Link | |
| 6,336,930 B1 * | 1/2002 | Stalcup et al. | |

* cited by examiner

Primary Examiner—Pedro Philogene
(74) Attorney, Agent, or Firm—Harness, Dickey & Pierce, P.L.C.

(57) ABSTRACT

A system for performing osteotomies includes a bone plate and a retractor assembly. The bone plate generally includes a first mounting portion for attachment to a first bone portion, a second mounting portion for attachment to a ssecond bone portion, and an intermediate portion connecting the first mounting portion and the second mounting portion. The retractor assembly includes first and second handle members coupled for relative movement about a first pivot axis and first and second jaw members coupled to the first and second handle members, respectively.

23 Claims, 8 Drawing Sheets

BONE PLATE AND RETRACTOR ASSEMBLY

FIELD OF THE INVENTION

The present invention relates generally to surgical osteotomies. More particularly, the present invention relates to a system for performing osteotomies including a bone plate and a retractor assembly. More specifically, but without restriction to the particular embodiment and/or use which is shown and described for purposes of illustration, the present invention relates to a system for performing osteotomies including a bone plate having a reduced width central portion and a retractor assembly having a pair of jaws.

BACKGROUND OF THE INVENTION

In various orthopedic surgical procedures, it is necessary to secure two bone portions in a relatively fixed relationship to each other. For example, such a secured relationship is required to mend a fracture which has occurred to the bone or to correct a malunion or deformity of the bone. To ensure that the bone can regenerate in the proper orientation and fuse properly, it is important that the bone portions be fixed in the desired position during bone regeneration.

Various external fixation devices for the repair of traumatized bone are known. For example, U.S. Pat. No. 5,662,650 to Bailey et al. discloses an apparatus for the external fixation of large bones. The apparatus is illustrated to include a main body as well as a first and second bone screw clamps. The main body serves to allow the apparatus to axially rotate, thereby providing a proper longitudinal rotational location of the bone screws with respect to a bone. The first bone screw clamp is used to secure a first bone screw to the apparatus while permitting the first bone screw to be axially displaced from the main body. In a similar fashion, the second bone screw clamp functions to secure a second bone screw to the apparatus and to allow the second bone screw to be axially displaced with respect to the main body.

For osteotomies, it is known to employ a bone plate for securing adjacent bone portions in a relatively fixed relationship to each other. For example, tibial osteotomies performed to correct certain deformities open a wedge in the bone which allows for proper anatomic limb alignment. The wedge is created by a cut made across the bone that leaves a portion to serve as a hinge. A gap is established between adjacent bone portions that is maintained by the bone plate secured to each of the bone portions.

While known systems for osteotomies such as tibial osteotomies have proven acceptable for certain applications, such systems are nevertheless susceptible to improvements that may enhance their performance.

SUMMARY OF THE INVENTION

An advantage of the present invention is the provision of a system for performing osteotomies which provides for improved access to the bone grafting site.

It is a related object of the present invention to provide a bone plate for osteotomies including a reduced width central portion for permitting improved access to the bone grafting site.

Another advantage of the present invention is the provision of a system for performing osteotomies including a bone plate with increased bone screw pull-out, compression, tension and torsional strength.

Another advantage of the present invention is the provision of a system for performing osteotomies including a retractor assembly permitting improved bone plate placement and improved anatomic limb alignment.

In one form, the present invention provides a bone plate for securing the relative positions between first and second bone portions of a bone separated by a gap. The bone plate includes a first mounting portion, a second mounting portion and an intermediate portion. The first mounting portion is for attachment to the first bone portion. The second mounting portion is for attachment to the second bone portion. The intermediate portion connects the first mounting portion and the second mounting portion in a first direction and has a reduced central width.

Additional advantages and features of the present invention will become apparent from the following description and appended claims, taken in conjunction with the accompanying drawings.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiment of the present invention is merely exemplary in nature and is in no way intended to limit the scope of the present invention or its application or uses.

Figure 1:
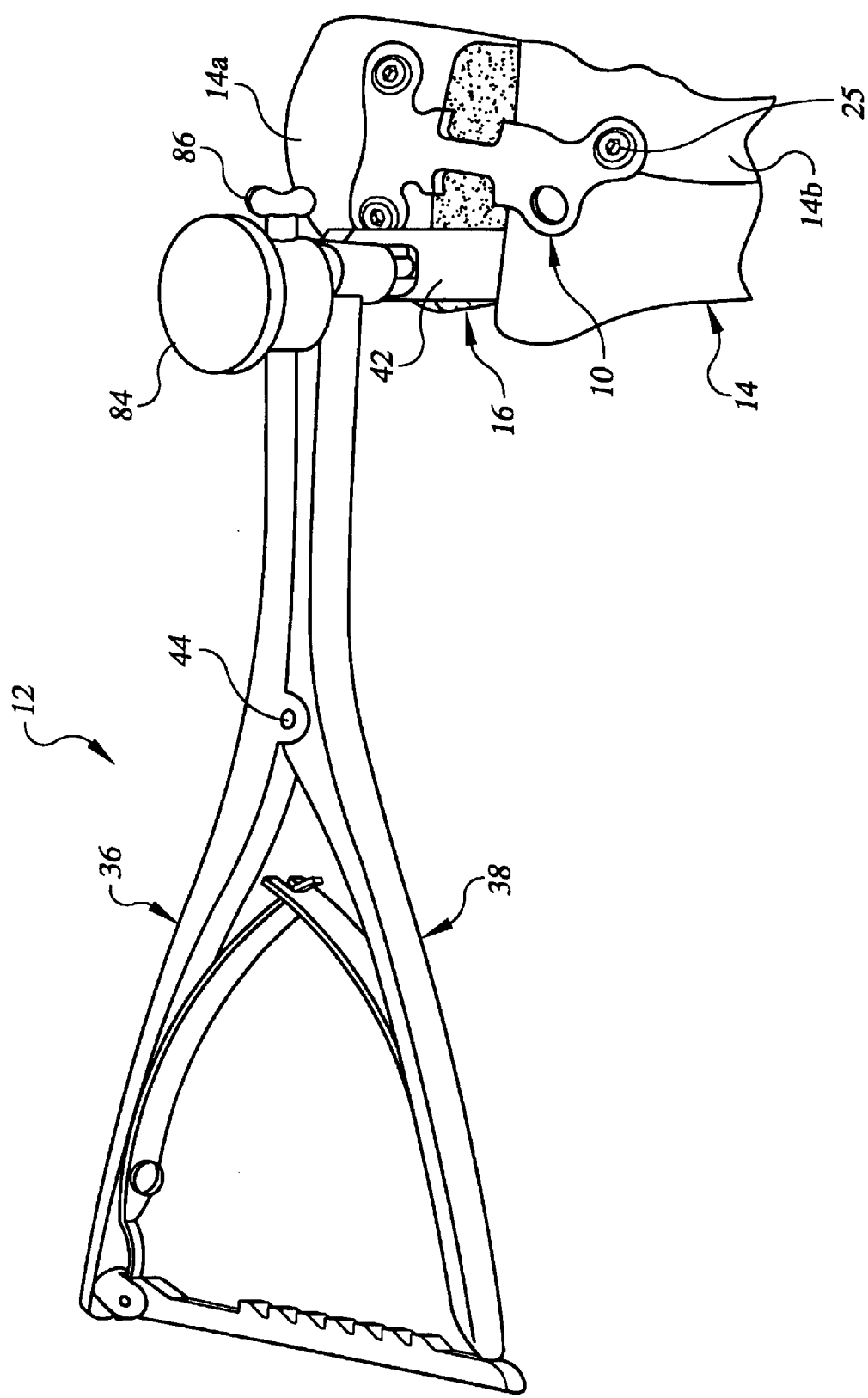
FIG. 1 is an environmental view illustrating a system for performing osteotomies in accordance with the teachings of a preferred embodiment of the present invention to include a first bone plate and a retractor assembly, the first bone plate and the retractor assembly are shown operatively associated with a tibia.

Referring initially to the environmental view of FIG. 1, a system for performing osteotomies constructed in accordance with the teachings of a preferred embodiment of the present invention is illustrated. The system is shown to generally include a first bone plate 10 and a retractor assembly 12. The bone plate 10 is shown attached to first and second portions 14a and 14b of a bone 14 for securing the relative positions between the first and second portions 14a and 14b which are separated by a wedge-shaped gap 16. The retractor assembly 12 is shown immediately prior to removal from the gap 16 after it has been used by a surgeon to establish a desired dimension for the gap 16 between the first and second bone portions 14a and 14b.

In the exemplary use shown in FIG. 1, the bone 14 is a tibia and the first bone plate 10 is being used to secure the relative positions between the first and second portions 14a and 14b for a high tibial osteotomy. Those skilled in the art will appreciate that the teachings of the present invention are applicable for other surgical procedures in which it is necessary to secure the relative positions between bone portions.

Figure 2A:
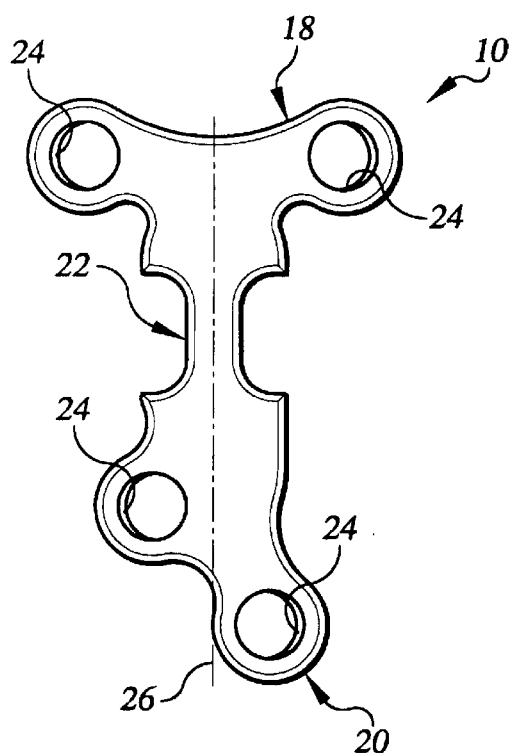
FIGS. 2A–2C are various views of the first bone plate of the preferred embodiment of the present invention.
Figure 2B:
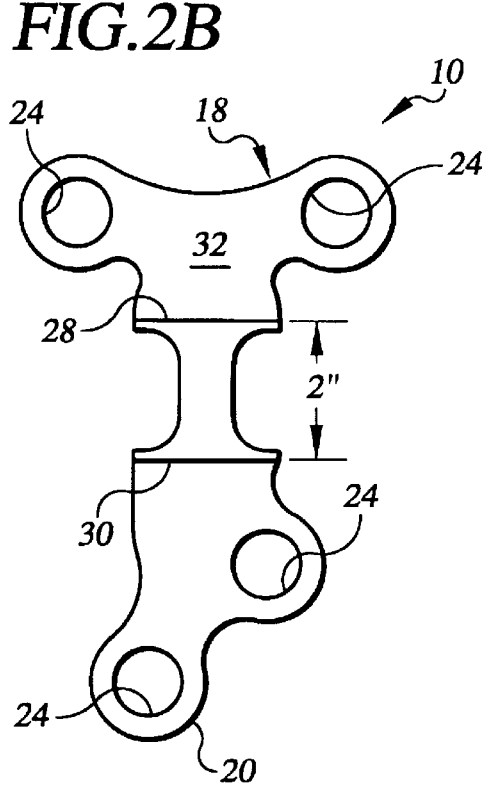
Figure 2C:
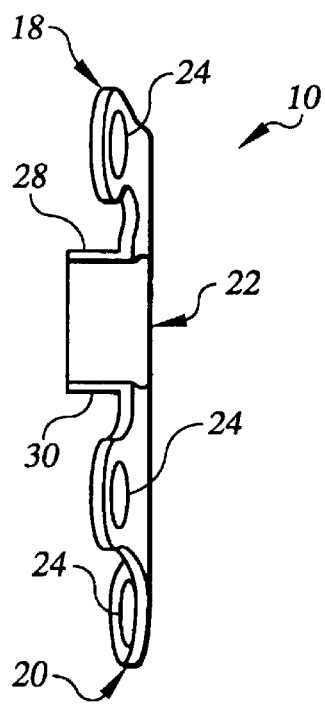

With continued reference to FIG. 1 and additional reference to FIGS. 2A–2C, the first bone plate 10 of the present invention will be further described. The first bone plate 10 is shown to generally include a first or upper mounting portion 18, a second or lower mounting portion 20 and an intermediate portion 22. The first mounting portion 18 is for attachment to the first bone portion 14a and the second mounting portion 20 is for attachment to the second bone portion 14b. The intermediate portion 22 connects the first mounting portion 18 and the second mounting portion 20. In the preferred embodiment, the first mounting plate 10 is unitarily constructed. One suitable material is titanium alloy. However, those skilled in the art will readily appreciate that other well known materials in the art may be employed.

The first bone plate 10 is shown to include a plurality of mounting apertures 24 each adapted to receive a fastener 25 for securing the bone plate 10 to the bone 14. In the embodiment illustrated, the first mounting portion 18 includes a pair of mounting apertures 24 having centers which are spaced apart from and on opposite sides of a longitudinally extending centerline 26 of the intermediate portion 22. In a similar manner, the second mounting portion 20 includes a pair of mounting apertures 24 having centers which are spaced apart from an opposite end on opposite sides of the centerline 26. In the preferred embodiment, the centers of the mounting apertures 24 of the second mounting portion 20 are also spaced apart from one another in a second direction which is generally parallel to the longitudinal centerline 26.

In the preferred embodiment, the first and second mounting portions 18 and 20 are shown to be curved in a direction perpendicular to the centerline 26. The spacing of the fasteners 25 increases the torsional and compressive stability of the bone plate 10 by spreading out the fasteners 25. The curvature of the mounting portions 18 and 20 increases the pullout strength of the first bone plate 10 by accommodating converging fasteners 25.

The first and second mounting portions 18 and 20 include first and second shelves 28 and 30, respectively, which extend from a rear surface 32 of the first bone plate 10. In the preferred embodiment, the first and second rearwardly extending shelves 28 and 30 are both disposed immediately adjacent the intermediate portion 22 and are defined by the intermediate portion which is generally I-shaped. The first and second shelves 28 and 30 define a flange for engaging the cortical bone of the first and second bone portions 14a and 14b, respectively. The distance between the first and second shelves is selected based upon the desired length of the gap. As shown particularly in FIG. 2B, the first and second shelves 28 and 30 preferably slope anteriorly at an angle of approximately 2°. The anterior slope allows a wider portion of the shelves 28 and 30 to be positioned posteriorly.

The intermediate portion 22 of the first bone plate 10 has a central section with a reduced cross-sectional area. In the embodiment illustrated, a central width of the intermediate portion in a direction perpendicular to the centerline 26 is substantially less than the width of the intermediate portion 22 adjacent first mounting portion 18 and adjacent the second mounting portion 22. In one application, the central width of the intermediate portion 22 is approximately 6 mm. The first and second shelves 28 and 30 preferably extend the entire width of the intermediate portion 22 adjacent the respective first and second mounting portions 18 and 20. As illustrated, a central section of the intermediate portion 22 and the first and second shelves 28 and 30 cooperate to define an I-beam shape. The reduced central width of the intermediate portion 22 of the bone plate 10 permits improved access to the bone grafting site within the gap 16. Additionally, the reduced central width of the intermediate portion 22 facilitates placement of the bone plate 10 and compaction of the bone graft (not shown).

The particular bone plate 10 illustrated in FIGS. 2A–2C is intended for a high tibial osteotomy of a left tibia. It will be understood by those skilled in the art that the teachings of the present invention are equally applicable for a high tibial osteotomy of the right tibia. In this alternative application, the bone plate 10 would be configured to be a mirror image about the centerline 26.

Figure 3:
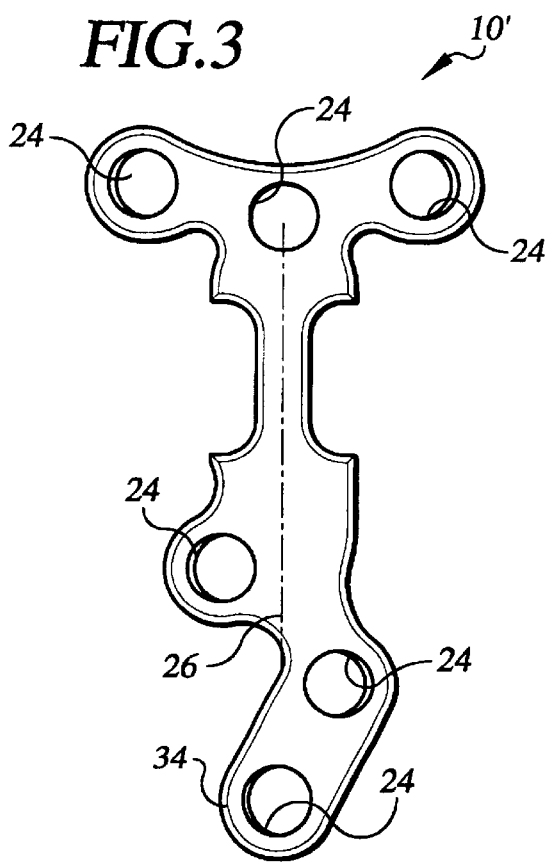
FIG. 3 is a front view of a second bone plate of the preferred embodiment of the present invention.

Turning now to FIG. 3, a second bone plate 10' of the system of the present invention is illustrated. The second bone plate 10' shares various features in common with the first bone plate 10. For this reason, like reference numerals have been used in FIG. 3 to identify substantially identical elements which have been previously introduced with respect to FIGS. 2A–2C. The second bone plate 10' is particularly configured for a left high tibial osteotomy. Again, a similar bone plate for a right high tibial osteotomy would have a mirror image about the longitudinally extending centerline 26.

The second bone plate 10' primarily differs from the first bone plate 10 in the number of mounting apertures 24 provided in each of the first and second mounting portions 18 and 20. As shown, the first and second mounting portions 18 and 20 include three mounting apertures 24 as opposed to two. It will be appreciated by those skilled in the art that the particular number of mounting apertures 24 may be varied within the scope of the present invention.

The additional mounting aperture 24 of the first mounting portion 18 is shown disposed between the other mounting apertures 24 and is generally centered along the centerline 26. With respect to the second mounting portion 20, the additional mounting aperture 24 is located in a downwardly extending segment 34 and has a center positioned laterally between the other two mounting apertures 24. In the embodiment illustrated, the additional mounting aperture 24 of the second bone plate 10' has a center generally aligned along the centerline 26.

Turning now to FIGS. 4A–4D through FIG. 8, the retractor assembly 12 of the present invention will now be further described. The retractor assembly 12 is shown to generally include a first or upper handle member 36 and a second or lower handle member 38. The retractor assembly 12 is further shown to generally include a first or upper jaw member 40 and a second or lower jaw member 42. The second handle member 38 is coupled to the first handle member 36 for relative movement about a first pivot axis 44.

The first jaw member 40 has a first end 46 coupled to a first end 48 of the first handle member 36. Similarly, the second jaw member 42 has a first end 50 coupled to a first end 52 of the second handle member 38. The second jaw member 42 includes a second end 54 pivotally coupled to a second end 56 of the first jaw member 40 for relative movement about a second pivot axis 58. In the preferred embodiment, the second pivot axis 58 is generally perpendicular to the first pivot axis 44.

The first end 46 of the first jaw 40 is illustrated to define a cavity 58. The cavity 58 adjustably receives a ball 60 attached to and extending from the first end 48 of the first arm 36. In an identical manner, the first end 50 of the second jaw 42 defines a cavity 58 receiving a ball 60 extending from the first end 52 of the second arm 38. The joints defined between the balls 60 and their respective cavities 58 accommodate relative rotation between the first and second jaws 40 and 42 and the first and second arms 36 and 38 about axes passing through the respective ball 60 and generally parallel to the second axis 58.

The retractor assembly 12 is further illustrated to include a coupling member 62 for maintaining a selected orientation between the first and second jaws 40 and 42 by maintaining a selected orientation between the first and second arms 36 and 38. In the embodiment illustrated, the coupling member 62 is attached to a second end 64 of the first handle member 36 and releasably engageable with a second end 66 of the second handle member 38. The coupling member 62 is pivotally attached to the second end 64 of the first handle member 36 for articulation about a pivot pin 68. The coupling member 62 is formed to include a plurality of ratchet teeth 70 along its length for engaging the second end 66 of the second handle 38 and preferably includes indicia indicative of a size of the gap 16 when the first and second jaws 40 and 42 are fully inserted into a cut between the first and second bone portions 14a and 14b. The indicia is shown particularly in FIG. 4D.

Figure 4A:
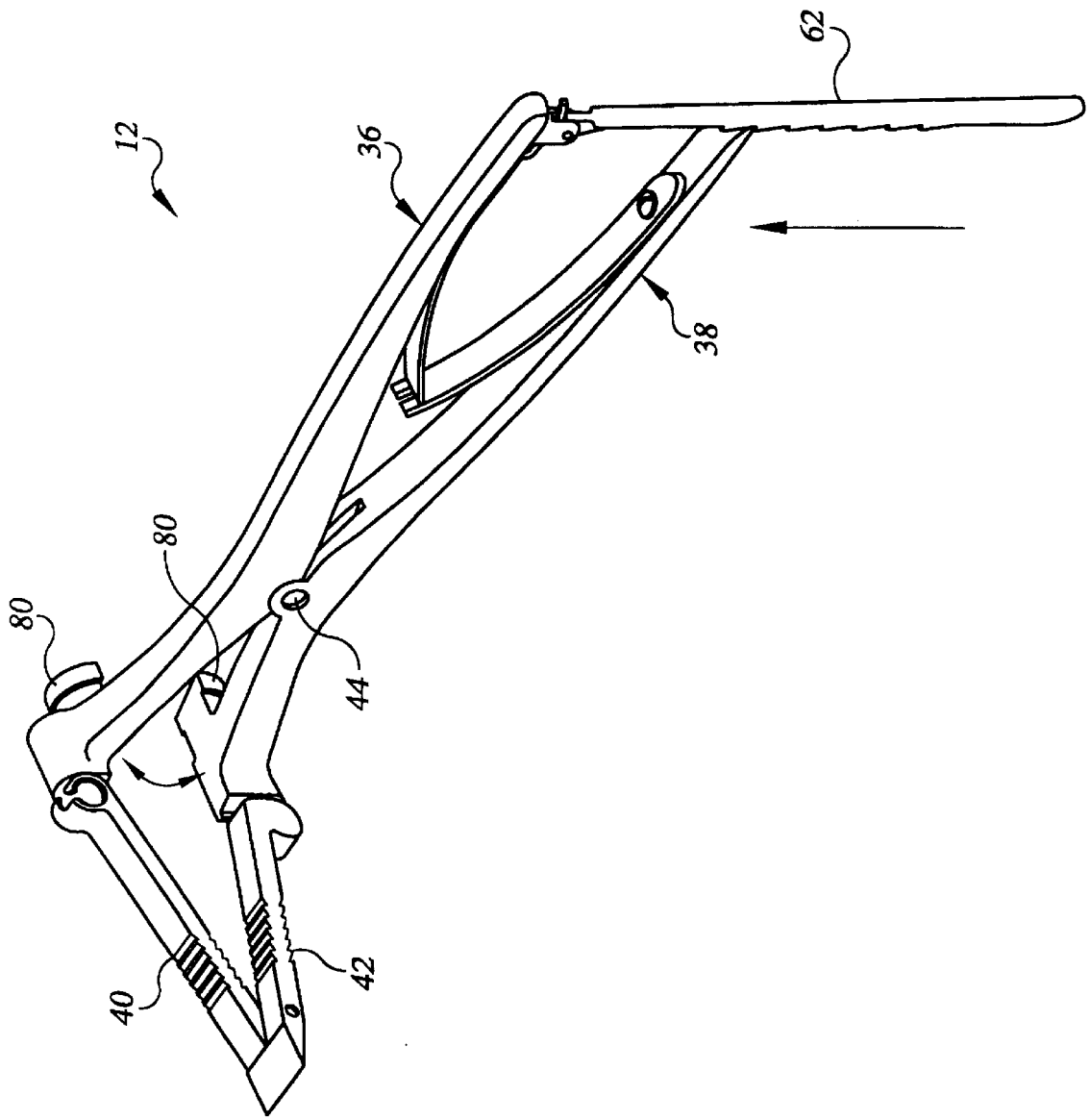
FIGS. 4A–4D are various views of the retractor assembly of the preferred embodiment of the present invention.
Figure 4B:
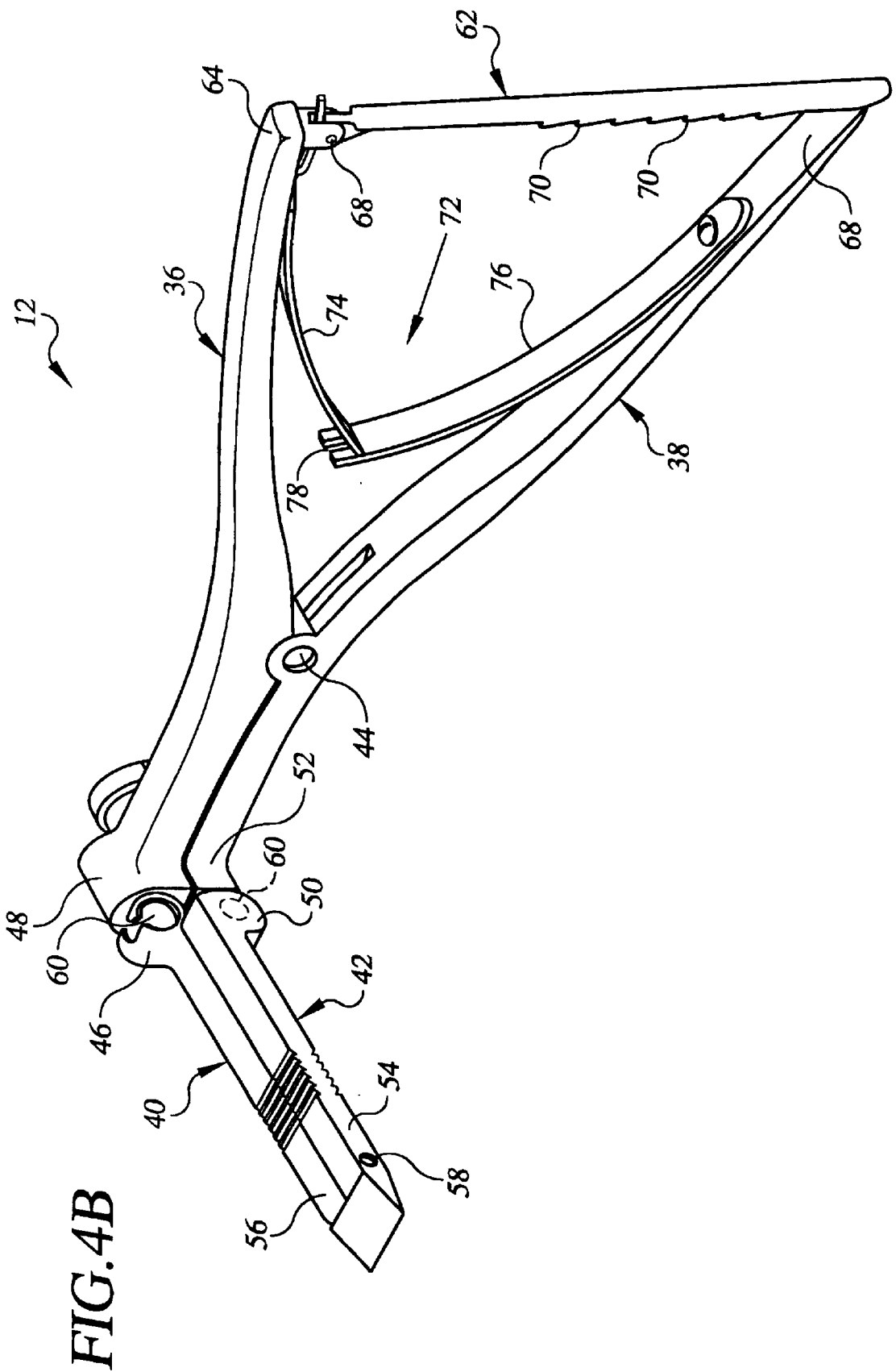
Figure 4C:
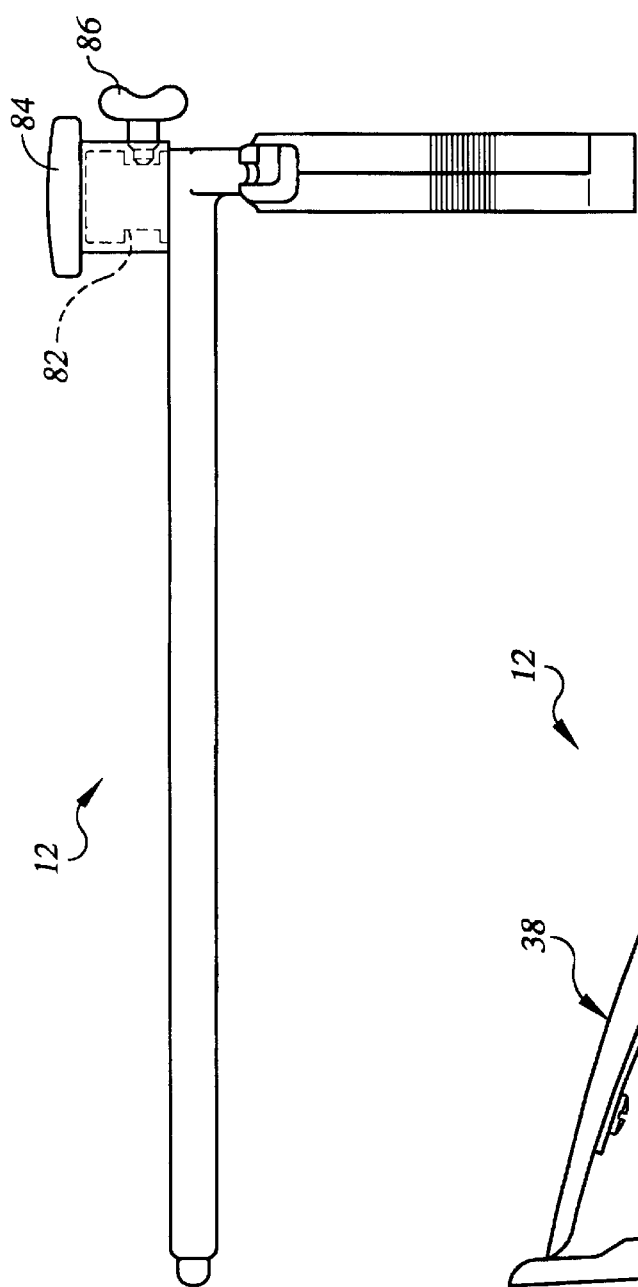
Figure 4D:
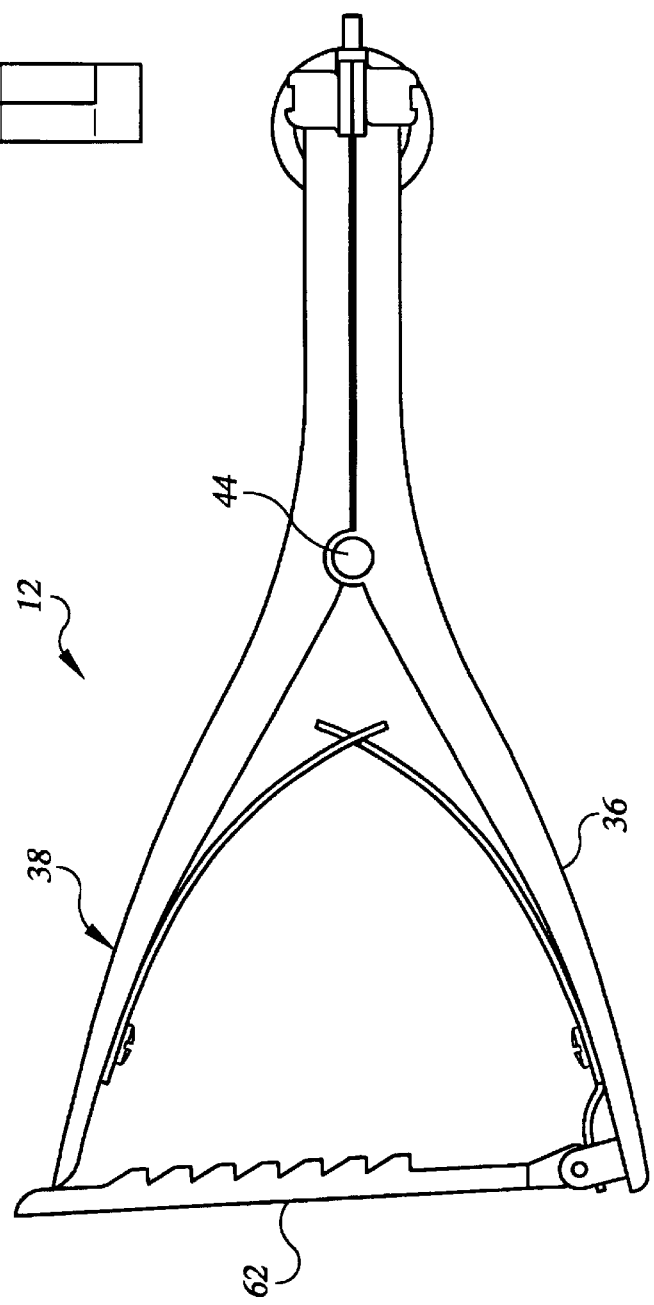
Figure 5:
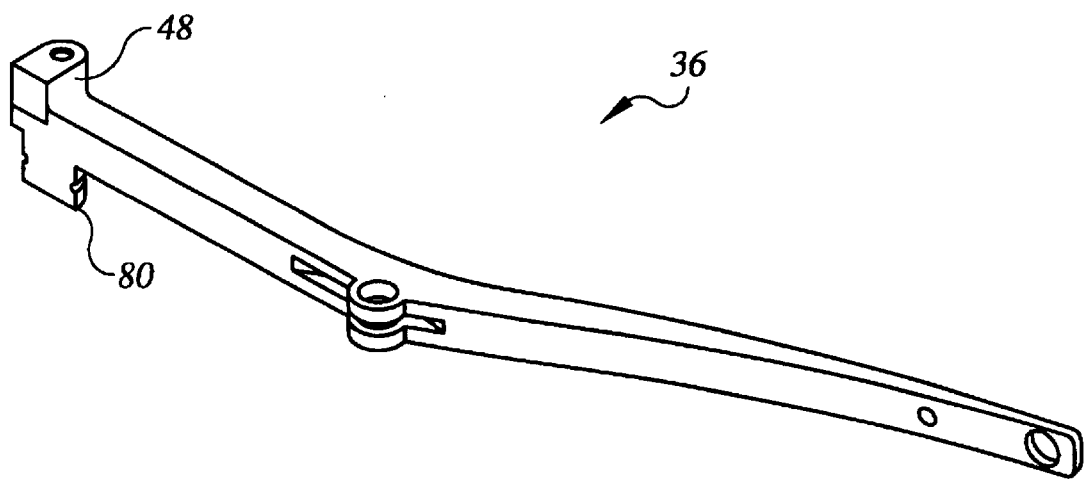
FIG. 5 is a perspective view of an upper handle of the retractor assembly of the preferred embodiment of the present invention.
Figure 6:
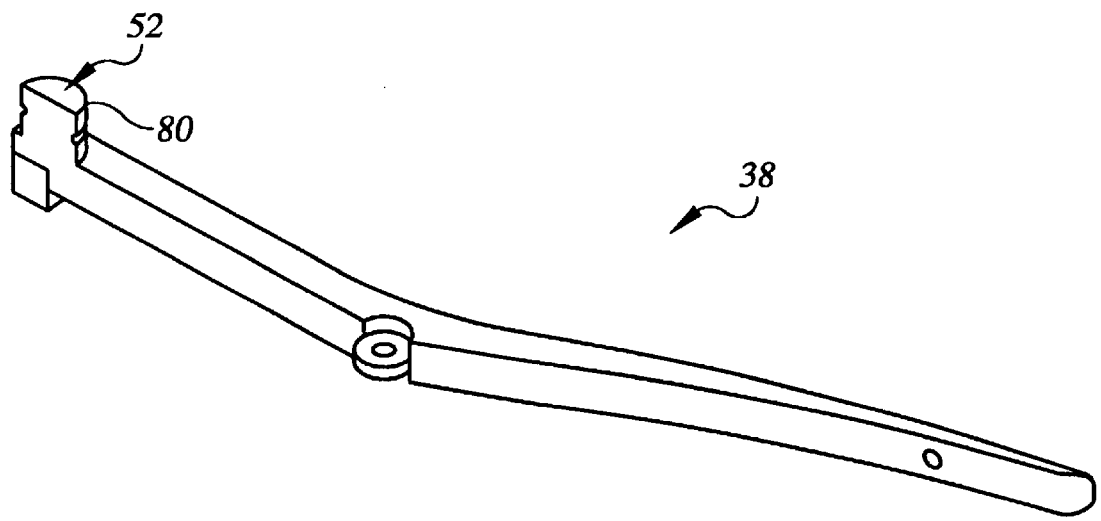
FIG. 6 is a perspective view of a lower handle of the retractor assembly of the preferred embodiment of the present invention.
Figure 7A:
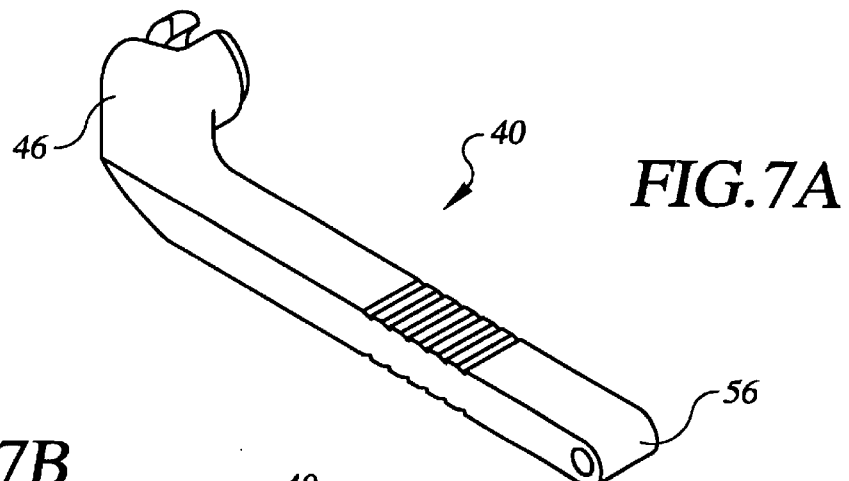
FIGS. 7A–7D are various views of an upper jaw of the retractor assembly of the preferred embodiment of the present invention.
Figure 7B:
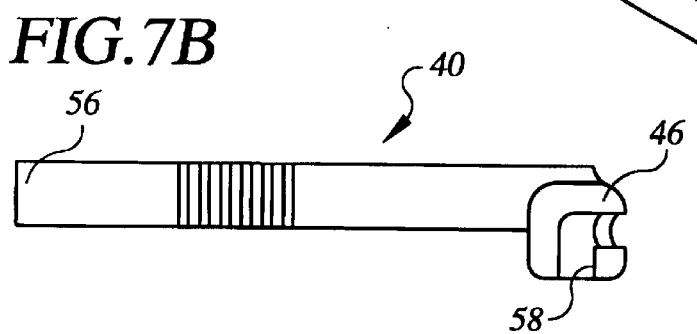
Figure 7C:
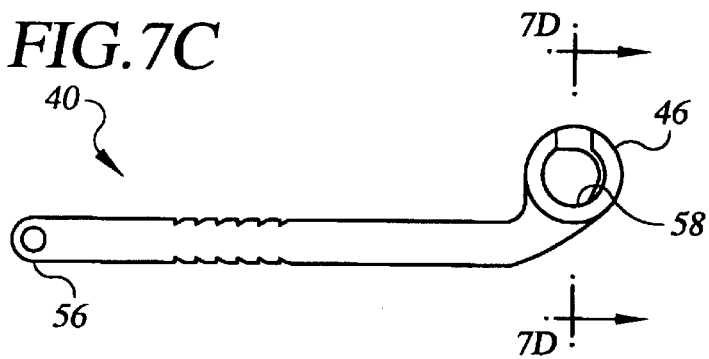
Figure 7D:
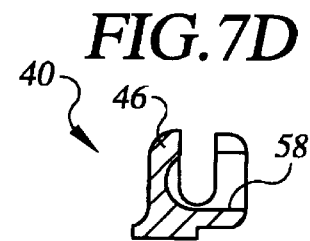
Figure 8:
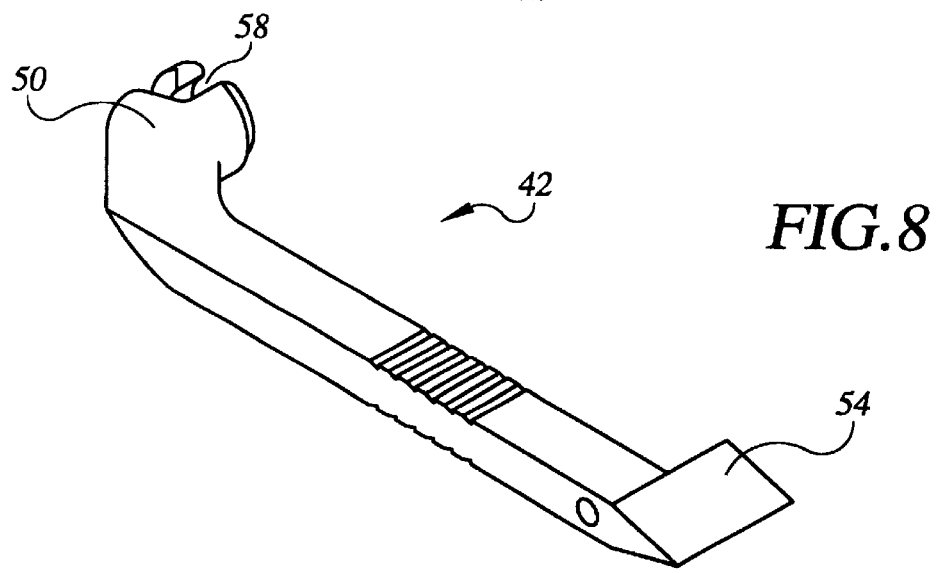
FIG. 8 is a perspective view of a lower jaw of the retractor assembly of the preferred embodiment of the present invention.

The retractor assembly 12 further includes a biasing arrangement 72 coupled to the first and second handle members 36 and 38 and operative for biasing the first and second jaw members 40 and 42 to a first position in which the first and second jaw members 40 and 42 are generally located in a common plane. The first position is illustrated in FIG. 4b. The biasing arrangement 72 is illustrated to include first and second spring members 74 and 76. The first spring member 74 is connected at one end to the first handle member 36. The second spring member 76 is similarly mounted at one end to the second handle member 38. One of the spring members 74 includes a slot 78 at its free end which receives the free end of the other spring member 76. Thus, the spring member 74 and 76 are arranged with the handle members 36 and 38, respectively, to provide a spring biasing arrangement for biasing the handle members 36 and 38 away from one another.

In operation, the first and second jaws 40 and 42 of the retractor assembly 12 are inserted into a cut between the first and second bone portions 14a and 14b while the first and second jaws 40 and 42 are substantially coplanar. In one application, the first and second jaws 40 and 42 are inserted to a depth of approximately 35 mm. The first ends 48 and 52 of the first and second handle members 36 and 38 both include a semicylindrical portion 80. Semicylindrical portions 80 cooperate to define a cylinder having a reduced width circumferential groove 82. A cap 84 defines a cylindrical aperture receiving the portions 80. The cap 84 is secured to the retractor assembly 12 through a thumb screw 86 and provides a surface for striking with a hammer during introduction of the jaws 40 and 42 into the bone 14.

A triangular shaped wedge is opened between the first and second bone portions 14a and 14b with the retractor assembly 12 through manual squeezing of the first end second handle members 36 and 38. The manual squeezing of the first and second handle members 36 and 38 overcomes the biasing force provided by the biasing arrangement 72 and urges the first end 48 of the first handle member 36 apart from the first end 52 of the second handle member 38. As a result, the first end 46 of the first jaw member and the first end 50 of the second jaw member 42 are urged apart through relative rotation about the second pivot axis 58 to a second position. The second position is shown, for example, in FIG. 4A.

The surgeon opens the gap in the bone 14 to a desired dimension. The gap 16 and the bone 14 corresponds in size to the indicia on the coupling member 62 located adjacent the second end 66 of the second handle member 38 based on complete insertion of the jaws 40 and 42. The configuration of and relative movement between the jaws 40 and 42 permit improved bone plate placement and anatomic limb alignment. When the desired gap 16 has been established, the bone plate 10 or 10' is secured in place with the fasteners 25 and the coupling member 62 may be disengaged from the second end 66 of the second handle 38. The biasing force of the biasing arrangement 72 returns the first and second jaws 40 and 42 to their generally coplanar orientation. At this point the jaws 40 and 42 may be removed from the gap 16.

With the bone plate 10 in place, bone grafting material is introduced into the gap 16. It will be appreciated that the gap 16 is spanned only by the reduced width central portion of the intermediate portion 22. As such, improved access to the bone grafting site is provided.

Figure 9A:
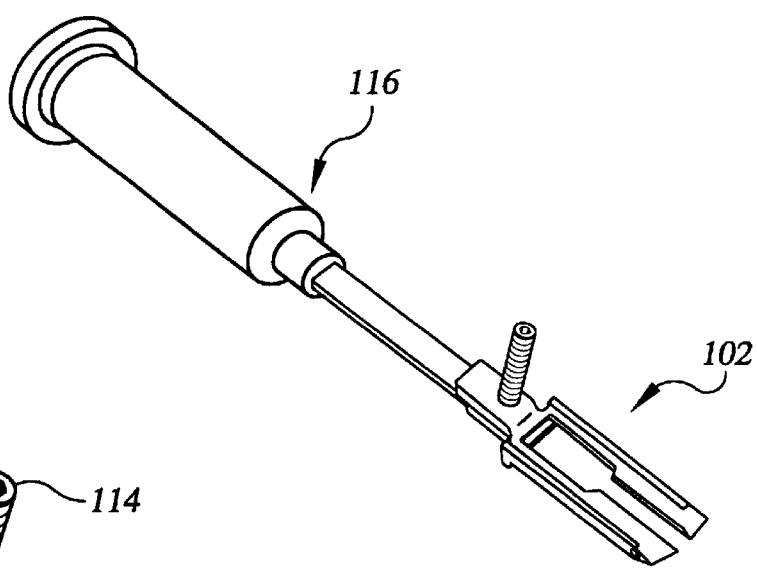
FIGS. 9A–9C are various views of a retractor assembly constructed in accordance with an alternative embodiment of the present invention.
Figure 9B:
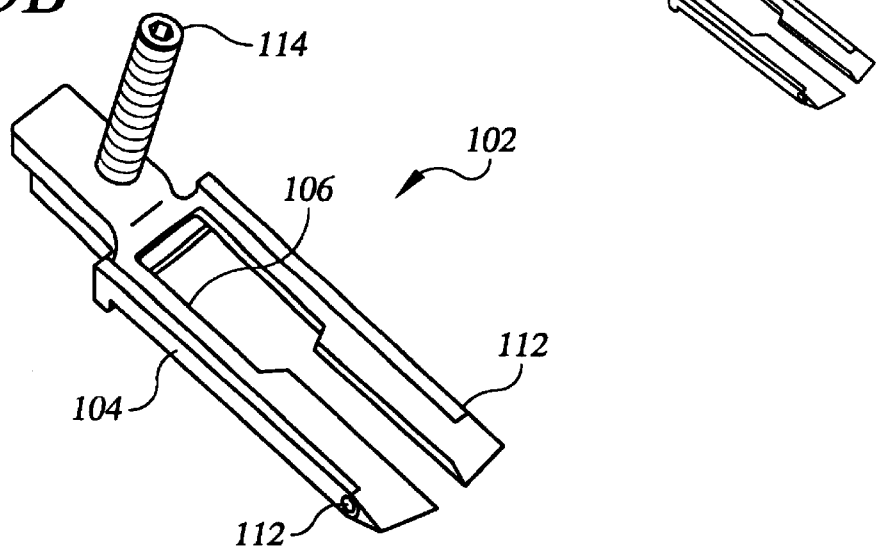
Figure 9C:
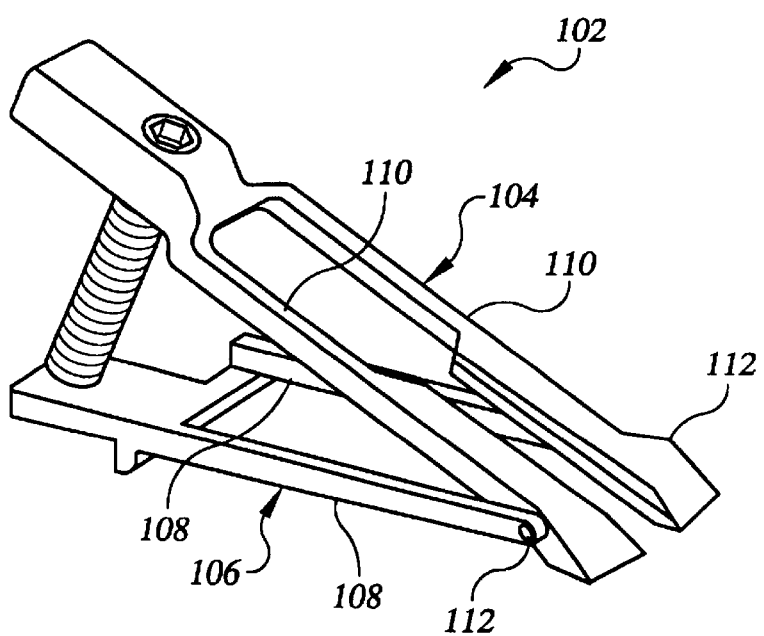

Turning now to FIGS. 9A–9C, a retractor assembly 102 constructed in accordance with the teachings of an alternative embodiment of the present invention is illustrated. The retractor assembly is shown to include an upper jaw 104 and a lower jaw 106. In the embodiment illustrated, the lower jaw 106 includes a pair of spaced apart arms 108 and the upper jaw similarly includes a pair of spaced apart arms 110. Forward ends of the arms 108 of the lower jaw 106 are coupled to an associated one of the arms 110 of the upper jaw 104 by a pin 112. The pins 112 define an axis about which the upper and lower jaws 104 and 106 relatively articulate between an open position and a closed position. The open position is shown in FIG. 9C and the closed position is shown in FIG. 9B.

The retractor assembly 102 is further shown to include a drive member 114 which threadably engages an aperture (not specifically shown) in an end of the upper jaw 104. Rotation of the drive member 14 in a first direction causes the drive member to extend below the upper jaw 104 and engage an end of the lower jaw 106. Through this engagement, the jaws 104 and 106 are articulated between the closed and open positions.

The retractor assembly 102 is shown in FIG. 9A engaged with a handle assembly 116. The handle assembly releasably engages the upper jaw 104 and provides a striking surface for introducing the retractor assembly 102 into a bone opening. The handle assembly 116 may releasably engage the retractor assembly in any manner well known in the art. For example, the handle assembly may engage an aperture or slot defined by the upper jaw 104. Alternatively, the handle assembly 116 can threadably engage the retractor assembly 102.

The foregoing discussion discloses and describes merely exemplary embodiments of the present invention. One skilled in the art will recognize from such discussion and from the accompanying drawings and claims, that various changes, modifications and variations can be made therein without departing from the spirit and scope of the invention.

What is claimed is:

1. A bone plate for securing the relative positions between first and second portions of a bone separated by a gap, the bone plate comprising:
   a first mounting portion for attachment to the first bone portion;
   a second mounting portion for attachment to the second bone portion; and
   an intermediate portion connecting the first mounting portion and the second mounting portion in a first direction, the intermediate portion having a reduced cross-sectional dimension and including first and second shelves extending from a rear surface of the bone plate, the first and second shelves each having a width in a direction generally parallel to the first direction that is substantially greater than a central portion of the intermediate portion.

2. The bone plate for securing the relative positions between first and second portions of a bone separated by a gap of claim 1, wherein the intermediate portion has a central portion with a width in a second direction perpendicular to the first direction that is substantially less than a width of a first end of the intermediate portion a width of a second end of the intermediate portion.

3. The bone plate for securing the relative positions between first and second portions of a bone separated by a gap of claim 1, wherein the first and second mounting portions both include a plurality of mounting apertures.

4. The bone plate for securing the relative positions between first and second portions of a bone separated by a gap of claim 3, wherein each of the mounting apertures includes a center spaced from a line coincident with a centerline of the intermediate portion.

5. The bone plate for securing the relative positions between first and second portions of a bone separated by a gap of claim 1, wherein the bone plate is curved in the second direction perpendicular to the first direction.

6. The bone plate for securing the relative positions between first and second portions of a bone separated by a gap of claim 1, wherein the first and second shelves are disposed immediately adjacent first and second ends of the intermediate portion, respectively.

7. The bone plate for securing the relative positions between first and second portions of a bone separated by a gap of claim 6, wherein one of the first and second mounting portions includes first and second mounting apertures spaced apart from one another in both the first direction and the second direction.

8. The bone plate for securing the relative positions between first and second portions of a bone separated by a gap of claim 1, wherein the reduced cross-sectional dimension is disposed between the first and second shelves.

9. The bone plate for securing the relative positions between first and second portions of a bone separated by a gap of claim 1, wherein the intermediate portion includes a segment linking the first and second shelves, the segment having a width substantially less than a width of the first and second shelves.

10. A bone plate for securing the relative positions between first and second portions of a bone separated by a gap, the bone plate comprising:
    a first mounting portion for attachment to the first bone portion;
    a second mounting portion for attachment to the second bone portion; and
    an intermediate portion connecting the first mounting portion and the second mounting portion in a first direction, the intermediate portion including first and second rearwardly extending shelves for extending into the gap and engaging the first and second portions of the bone, respectively, the first and second rearwardly extending shelves converge toward each other in a second direction, the second direction being generally perpendicular to the first direction.

11. The bone plate for securing the relative positions between first and second portions of a bone separated by a gap of claim 10, wherein the intermediate portion includes upper and lower surfaces defining the first and second rearwardly extending shelves, respectively.

12. The bone plate for securing the relative positions between first and second portions of a bone separated by a gap of claim 10, wherein the intermediate portion includes a central section having a reduced horizontal cross-sectional dimension.

13. The bone plate for securing the relative positions between first and second portions of a bone separated by a gap of claim 12, wherein the central section and the first and second rearwardly extending shelves cooperate to define an I-beam shape in which the first and second shelves are substantially wider than the central section.

14. The bone plate for securing the relative positions between first and second portions of a bone separated by a gap of claim 10, wherein the first and second shelves converge toward one another in an anterior direction.

15. The bone plate for securing the relative positions between first and second portions of a bone separated by a gap of claim 10, wherein the reduced cross-sectional dimension is disposed between the first and second shelves.

16. The bone plate for securing the relative positions between first and second portions of a bone separated by a gap of claim 10, wherein the intermediate portion includes a segment linking the first and second shelves, the segment having a width substantially less than a width of the first and second shelves.

17. A bone plate for securing the relative positions between first and second portions of a bone separated by a gap, the bone plate comprising:
    a first mounting portion for attachment to the first bone portion;
    a second mounting portion for attachment to the second bone portion; and
    an intermediate portion connecting the first mounting portion and the second mounting portion in a first direction, the intermediate portion having a reduced cross-sectional dimensions the first and second shelves disposed immediately adjacent first and second ends of the intermediate portion, respectively, the intermediate portion includes a segment linking the first and second shelves, the segment having a width substantially less than a width of the first and second shelves.

18. The bone plate for securing the relative positions between first and second portions of a bone separated by a gap of claim 17, wherein the intermediate portion has a central portion with a width in a second direction perpendicular to the first direction that is substantially less than a width of a first end of the intermediate portion a width of a second end of the intermediate portion.

19. The bone plate for securing the relative positions between first and second portions of a bone separated by a gap of claim 17, wherein the first and second mounting portions both include a plurality of mounting apertures.

20. The bone plate for securing the relative positions between first and second portions of a bone separated by a gap of claim 19, wherein each of the mounting apertures includes a center spaced from a line coincident with a centerline of the intermediate portion.

21. The bone plate for securing the relative positions between first and second portions of a bone separated by a gap of claim 17, wherein the bone plate is curved in the second direction perpendicular to the first direction.

22. The bone plate for securing the relative positions between first and second portions of a bone separated by a gap of claim 17, wherein one of the first and second mounting portions includes first and second mounting apertures spaced apart from one another in both the first direction and the second direction.

23. The bone plate for securing the relative positions between first and second portions of a bone separated by a gap of claim 17, wherein the reduced cross-sectional dimension is disposed between the first and second shelves.

* * * * *